(12) United States Patent
Miller et al.

(10) Patent No.: US 8,105,274 B2
(45) Date of Patent: *Jan. 31, 2012

(54) CATHETER INCORPORATING A HIGH COLUMN STRENGTH DISTAL TIP REGION

(75) Inventors: Paul J. Miller, St. Paul, MN (US); Tracee E. J. Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/848,673

(22) Filed: Aug. 2, 2010

(65) Prior Publication Data
US 2010/0298859 A1 Nov. 25, 2010

Related U.S. Application Data

(63) Continuation of application No. 10/876,815, filed on Jun. 25, 2004, now Pat. No. 7,766,869, which is a continuation of application No. 09/898,685, filed on Jul. 3, 2001, now Pat. No. 6,761,703.

(51) Int. Cl.
*A61M 29/00* (2006.01)

(52) U.S. Cl. ............. 604/103; 604/96.01; 604/915; 606/192

(58) Field of Classification Search ........... 604/915, 604/101.04, 96.01, 102.01, 93.01, 103, 103.04, 604/103.05; 606/192, 194
See application file for complete search history.

(56) References Cited

U.S. PATENT DOCUMENTS

| | | |
|---|---|---|
| 3,435,826 A | 4/1969 | Fogarty |
| 4,884,579 A | 12/1989 | Engelson |
| 4,899,729 A | 2/1990 | Gill et al. |
| 4,921,479 A | 5/1990 | Grayzel |
| 5,047,045 A | 9/1991 | Arney et al. |
| 5,156,594 A | 10/1992 | Keith |
| 5,192,295 A * | 3/1993 | Danforth et al. ............. 606/194 |
| 5,221,270 A | 6/1993 | Parker |
| 5,334,148 A | 8/1994 | Martin |
| 5,370,616 A | 12/1994 | Keith et al. |
| 5,447,503 A | 9/1995 | Miller |
| 5,447,506 A | 9/1995 | Lindquist |
| 5,573,508 A | 11/1996 | Thronton |
| 5,728,063 A | 3/1998 | Preissman et al. |
| 5,728,067 A | 3/1998 | Enger |
| 5,755,704 A | 5/1998 | Lunn |

(Continued)

FOREIGN PATENT DOCUMENTS
EP 0462482 A1 12/1991
(Continued)

*Primary Examiner* — Kevin C Sirmons
*Assistant Examiner* — Deanna K Hall
(74) *Attorney, Agent, or Firm* — Seager, Tufte & Wickhem, LLC

(57) ABSTRACT

A catheter is disclosed providing a balloon catheter having a distal tip that is flexible while additionally incorporating high column strength. The present invention additionally provides a distal tip region that accommodates for various sized guidewires. In preferred embodiments, the distal tip region is initially configured for accommodating the passage of 0.12-inch guidewires only. Through specific manufacturing processes, however, the distal tip is modified so that it also may be expanded to accommodate the passage of 0.14-inch guidewires. In additional preferred embodiments, an elastomeric sleeve is disposed over the modified distal tip to allow the tip to return to the initial 0.12-inch accommodating profile when the larger 0.14-inch guidewire is withdrawn from the catheter.

17 Claims, 2 Drawing Sheets

U.S. PATENT DOCUMENTS

| | | | |
|---|---|---|---|
| 5,769,819 A * | 6/1998 | Schwab et al. | 604/103 |
| 5,810,867 A | 9/1998 | Zarbatany et al. | |
| 5,827,225 A | 10/1998 | Ma Schwab | |
| 5,891,110 A | 4/1999 | Larson et al. | |
| 6,129,707 A | 10/2000 | Cryer | |
| 6,135,992 A | 10/2000 | Wang | |
| 6,196,995 B1 | 3/2001 | Fagan | |
| 6,245,053 B1 | 6/2001 | Benjamin | |
| 6,517,515 B1 | 2/2003 | Eidenschink | |
| 6,648,854 B1 | 11/2003 | Patterson et al. | |
| 6,761,703 B2 | 7/2004 | Miller et al. | |
| 2004/0030319 A1 | 2/2004 | Korkor et al. | |

FOREIGN PATENT DOCUMENTS

| | | |
|---|---|---|
| WO | 99/44666 A2 | 9/1999 |
| WO | 01/15763 A1 | 3/2001 |

* cited by examiner

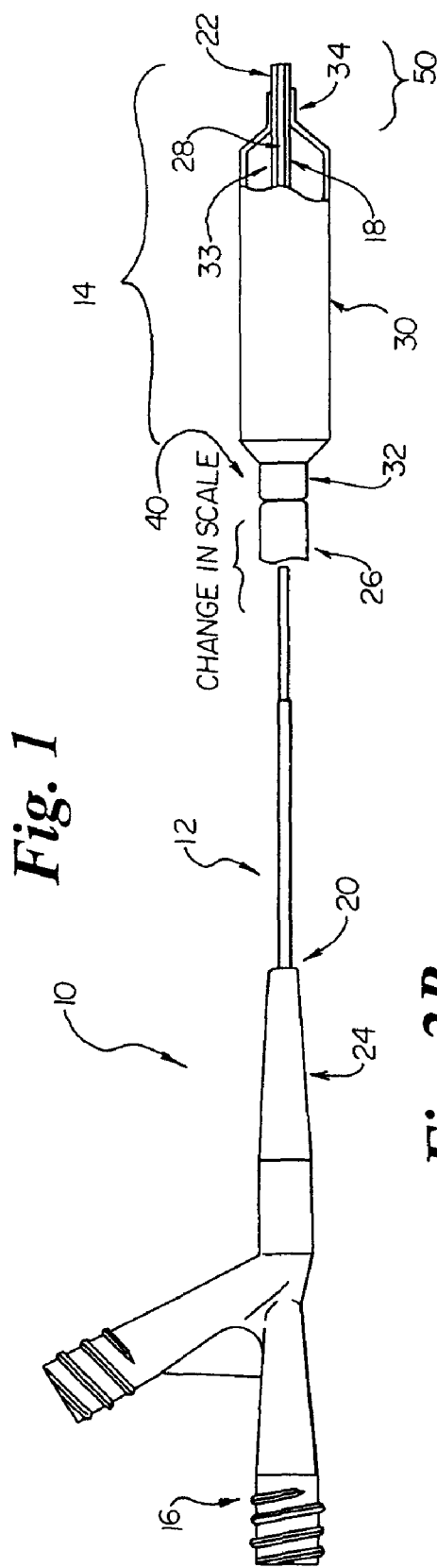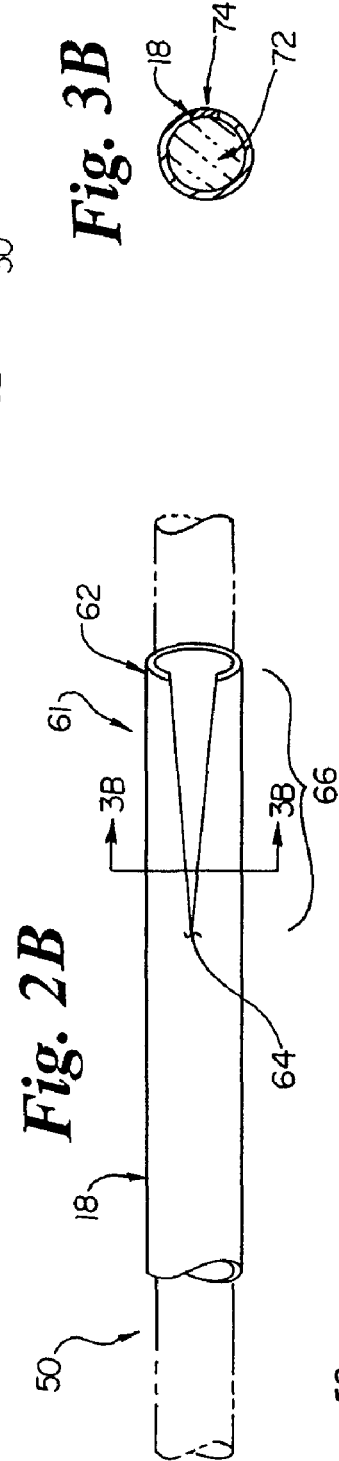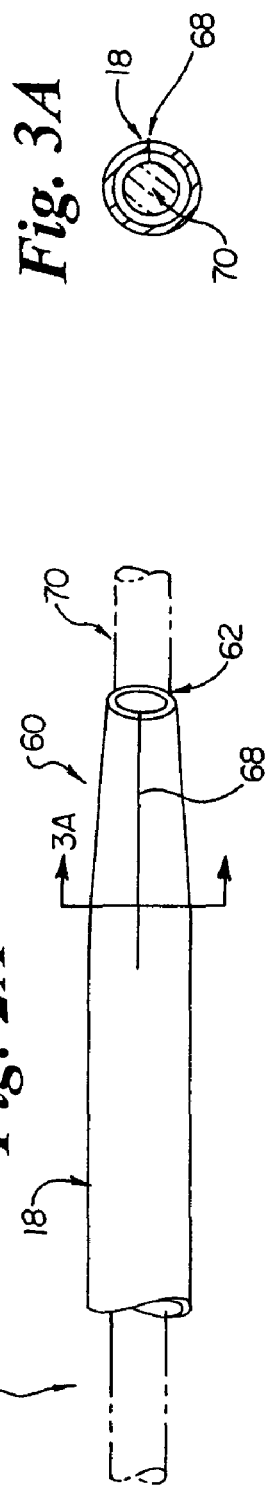

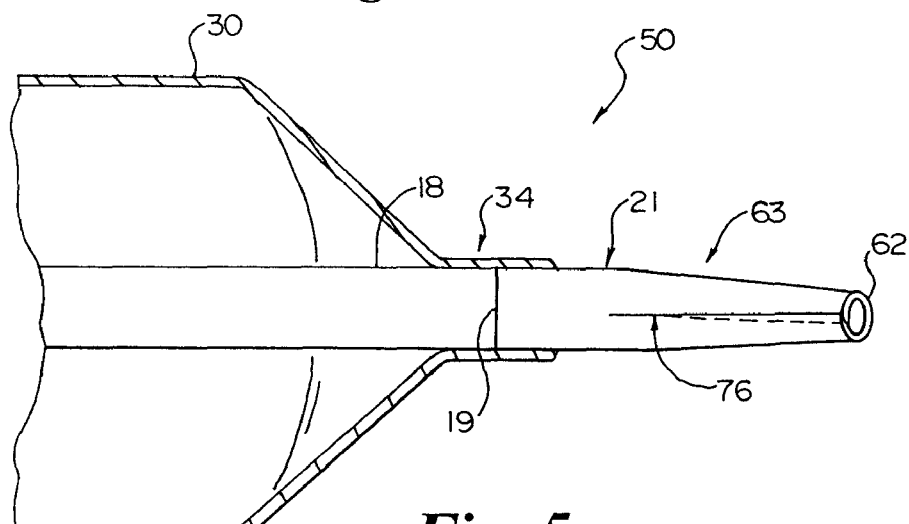
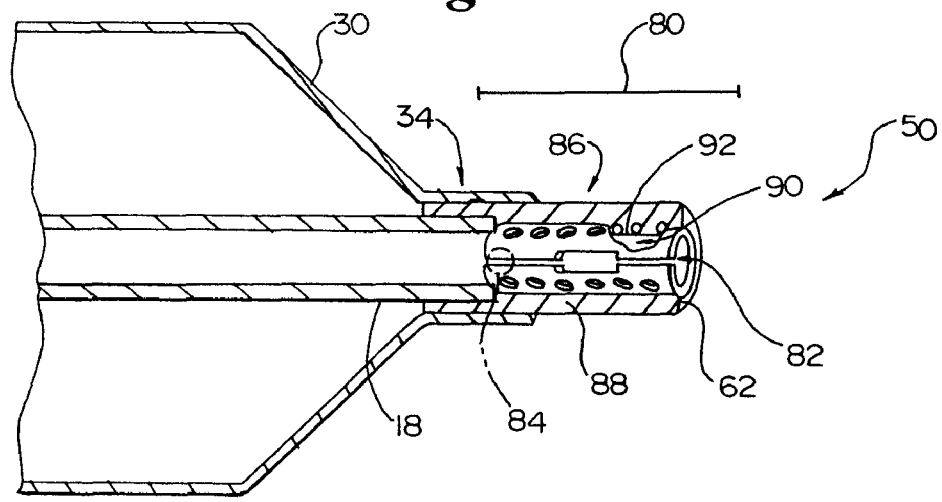
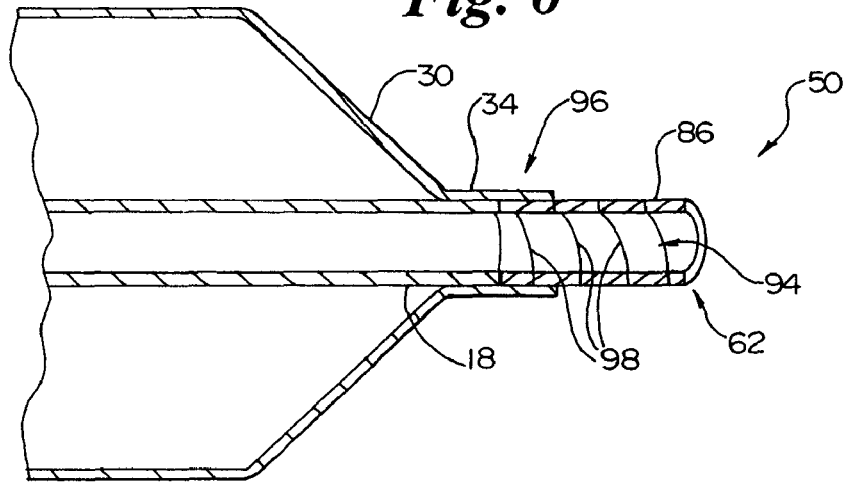

CATHETER INCORPORATING A HIGH COLUMN STRENGTH DISTAL TIP REGION

CROSS REFERENCE TO RELATED APPLICATIONS

This application is a continuation of co-pending U.S. application Ser. No. 10/876,815, filed Jun. 25, 2004, which is a continuation of U.S. application Ser. No. 09/898,685, filed Jul. 3, 2001, now U.S. Pat. No. 6,761,703, the entire disclosures of which are incorporated herein by reference.

TECHNICAL FIELD

The present invention generally relates to the field of intravascular medical devices used in combination with various sized guidewires. More specifically, the present invention relates to intravascular balloon dilation catheters using guidewires for crossing occluded stenotic regions, wherein the distal tip region of the balloon dilation catheter incorporates an expandable high column strength distal tip that accommodates an exchange for a larger diameter guidewire.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve the use of a balloon catheter with a guidewire, possibly in combination with other intravascular devices such as stents. A typical balloon catheter has an elongated shaft with a balloon attached proximate the distal end and a manifold attached to the proximal end. In use, the balloon catheter is advanced over the guidewire such that the balloon is positioned adjacent a restriction in a diseased vessel. The balloon is then inflated and the restriction in the vessel is opened.

There are three basic types of intravascular catheters for use in such procedures, including fixed-wire (FW) catheters, over-the-wire (OTW) catheters and single-operator-exchange (SOE) catheters. The general construction and use of FW, OTW and SOE catheters are all well known in the art. An example of an OTW catheter may be found in commonly assigned U.S. Pat. No. 5,047,045 to Arney et al. An example of an SOE balloon catheter is disclosed in commonly assigned U.S. Pat. No. 5,156,594 to Keith.

Several characteristics that are important in intravascular catheters include pushability, trackability and crossability. Pushability refers to the ability to transmit force from the proximal end of the catheter to the distal end of the catheter. Trackability refers to the ability to navigate tortuous vasculature. Crossability refers to the ability to navigate the balloon catheter across narrow restrictions in the vasculature, such as stenosed vessels or fully and partially deployed stents.

The trackability of a particular catheter design is analyzed in terms of the trackability of the distal portion of the catheter. The distal portion is the section of the catheter that must track the guidewire through the small tortuous vessels of a patient's vasculature. The size of the distal tip, the flexibility of the distal tip, and lumen diameter all influence the trackability of a catheter. Imparting more flexibility to the distal portion of a catheter, in particular, has been found to improve trackability. Increasing the flexibility within the distal tip improves handling and navigation over a guidewire.

To maximize crossability, the present invention is a catheter having a distal tip incorporating high column stiffness. Longitudinal column stiffness permits the distal portion of a catheter to cross narrow lesions within the vasculature. Flexible distal tips can yield to the pressures required to cross such lesions, thereby rendering the catheter ineffective. Further crossability is improved by the physician withdrawing the thinner, more flexible guidewire, and replacing it with a thicker and stiffer guidewire. Thicker guidewires add desirable stiffness when crossing tight or totally occluded lesions within the vasculature. Passage across such lesions often requires a greater longitudinal stiffness than a thinner guidewires affords. Advancing a thicker guidewire over the distal tip achieves this required longitudinal stiffness. Many catheter designs, however, cannot accommodate the replacement of a thicker guidewire. Often, the thicker guidewire is prevented from advancing through a catheter's distal-most tip that is designed specifically for thinner guidewires. The smaller distal tip openings of these catheters allow for easier navigation when used in combination solely with thinner gauge guidewires.

SUMMARY OF THE INVENTION

The present invention overcomes many of the disadvantages of the prior art by providing a balloon catheter having a distal tip that is sufficiently flexible, while additionally incorporating high column strength. Additionally, the present invention provides for a balloon dilation catheter that is accommodating to both thinner and thicker gauge guidewires, depending upon the desired use.

Flexibility in the distal tip region is necessary in order to navigate the tortuous vasculature within a patient's body. A delicate balance is required, however, between making the distal tip adequately flexible for navigation and making the distal tip adequately stiff for traversing tight lesions. A catheter that can easily reach a desired region deep within a patient's body is useless if the catheter cannot cross the region to treat the diseased area. In effect, the advantages of a flexible and nimble distal tip are diminished if the catheter otherwise becomes functionless.

The present invention provides a distal tip region of a catheter that strikes a balance that negligibly decreases the flexibility of the distal tip, yet enhances the column stiffness in the same. Using various combinations of material, in various arrays and configurations, several embodiments are disclosed having the desired flexibility and stiffness requirements for a distal tip region.

The present invention additionally provides for a distal tip region that accommodates for various sized guidewires. In preferred embodiments, the distal tip region is initially configured for accommodating the passage of a 0.012-inch guidewire or a 0.018-inch guidewire. Through specific manufacturing processes, however, the distal tip is modified so that it also may be expanded during use to accommodate the passage of selected larger diameter guidewires such as a 0.014-inch, a 0.018-inch, or a 0.035-inch guidewire through the original passage for the 0.012-inch guidewire. Further, in embodiments designed to initially accommodate a 0.018-inch guidewire, the distal tip is modified so that it can accommodate selected larger diameter guidewires such as a 0.035-inch guidewire. In certain embodiments, the distal tip region is expandable from about 0.012 inches to about 0.024 inches, preferably to about 0.020 inches, although other ranges can be selected such as expanding to about 0.038 inches to accommodate a 0.035-inch guidewire or smaller. In additional preferred embodiments, an elastomeric sleeve is disposed over the modified distal tip to allow the tip to return to the initial 0.012-inch or 0.018-inch accommodating profile when the larger 0.014-inch, 0.018-inch, or 0.035-inch guidewire is withdrawn from the catheter.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a partial cross-sectional plan view of a catheter in accordance with the present invention, having a distal tip region incorporating a high column strength inner shaft;

FIG. 2A is a partial perspective view of a preferred distal tip region of the catheter of FIG. 1, illustrating a slit along a portion of the inner shaft forming a tapered distal most tip and a guidewire extending therethrough;

FIG. 2B is a partial perspective view of the preferred distal tip region of FIG. 2A, illustrating the opening of the bond forming the tapered distal most tip when a larger guidewire is inserted therethrough;

FIG. 3A is a cross-sectional view along 3A-3A of the tapered distal tip of FIG. 2A, showing the positioning of the slit along the inner tubular member using a smaller diameter guidewire;

FIG. 3B is a cross-sectional view along 3B-3B of the tapered distal tip of FIG. 2B, showing the positioning and relationship of the slit along the shaft after exchanging the guidewire in FIG. 3A with a larger diameter guidewire;

FIG. 4 is a partial perspective view of an alternative distal tip, having a tapered end formed by overlapping a portion of the inner tubular member being slit from the distal most end;

FIG. 5 is a partial perspective view of another embodiment of the present invention, having a distal tip region incorporating a rigid polymeric insert having a slit extending along at least a portion of its length fitted within a portion of the inner tubular member; and FIG. 6 is a partial perspective view of another embodiment of the present invention, having a distal tip region incorporating a helical cut rigid polymeric insert abutting the distal end of the inner tubular member.

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Examples of construction, materials, dimensions, and manufacturing processes are provided for selected elements. All other elements employ that which is known to those skilled in the field of the invention. Those skilled in the art will recognize that many of the examples provided have suitable alternatives that may be utilized.

Referring now to the drawings, FIG. 1 is a cross-sectional view of an over-the-wire (OTW) balloon catheter, which is representative of one type of catheter that can incorporate the present invention. Other intravascular catheter embodiments are additionally suitable without deviating from the spirit and scope of the present invention. For example, intravascular catheters suitable for incorporating the present invention include fixed-wire (FW) catheters and single-operator-exchange (SOE) catheters.

The balloon catheter 10 includes a shaft assembly 12 and a balloon assembly 14 connected proximate the distal end of shaft assembly 12. A conventional OTW-type manifold assembly 16 is connected to the proximal end of the shaft assembly 12. The shaft assembly 12 includes an inner tubular member 18 having a proximal end 20 and a distal end 22. The proximal end 20 of the shaft assembly 12 extends into a manifold assembly 16 and is affixed thereto. A polyurethane strain relief 24 is snap-fit to the manifold assembly 16, and the shaft assembly 12 extends into the manifold assembly 16 through the polyurethane strain relief 24. An outer tubular member 26 is co-axially disposed about the inner tubular member 18 to define an annular inflation lumen therebetween.

Generally, outer tubular member 26 has an outer diameter ranging from 0.040 inches to 0.045 inches with a wall thickness ranging from 0.0028 inches to 0.0044 inches. Materials used to form outer tubular member 26 may vary depending upon the stiffness desired for the shaft assembly 12. Nylon and similar polyamides such as Vestimid or Grilamid are particularly suitable for rigid outer tubular members. Other suitable materials for a rigid outer tubular member include polyetheretherketone (PEEK), polyimide (PI), and polyetherimide (PEI). Rigidity may additionally be imparted to the outer tubular member 26 by incorporating a braid on or within the tubular member. Polyether block amide (PEBA), in contrast to the rigid polyamides, is a relatively flexible polymeric material having a durometer of approximately 70 D. Finally, the use of a polyamide such as CRISTAMID (available from Elf Atochem) imparts a slightly less rigid durometer than the rigid polyamids and slightly greater than the flexible PEBA material.

The inner tubular member 18 defines a guidewire lumen 28, which provides a passage for a guidewire (not shown). The inner tubular member 18 is generally made of polyethylene such as Marlex HDPE. In alternative embodiments, the inner tubular member 18 is made of a lubricious material such as polytetrafluoroethylene (PTFE). At the proximal end of the inner tubular member 18, the inner tubular member 18 has an outside diameter ranging from 0.022 inches to 0.030 inches, and most preferably about 0.025 inches. In one preferred embodiment, the inner diameter of the inner tubular member 18 measures approximately 0.018 inches to 0.023 inches, allowing for a 0.014-inch or 0.018-inch guidewire. The inner tubular member 18 has a wall thickness ranging from 0.0026 inches to 0.004 inches, and most preferably about 0.0032 inches for a 0.014-inch or 0.018-inch lumen. Alternative lumen diameters can be selected for accommodating other guidewire sizes. The outside diameter-to-wall thickness ratio must be sufficiently small to minimize the propensity for the shaft assembly 12, and more specifically the inner tubular member 18, from kinking.

Balloon assembly 14 includes a balloon body portion 30 with a proximal balloon waist 32 and a distal balloon waist 34. The proximal balloon waist 32 is connected to the outer tubular member 26 near its distal end 40 by means of an adhesive, or alternatively, by thermal bonding. The distal balloon waist 34 is connected to the inner tubular member 18 near its distal end 22 by means of an adhesive bond or a thermal bond such that the interior of the balloon 33 is in fluid communication with the annular inflation lumen.

FIGS. 2-6 show embodiments incorporating various designs within the distal tip region 50 of the catheter 10 of FIG. 1. In general, flexibility in the distal tip region 50 increases tracking performance within the tortuous vasculature of a patient. The distal tip region 50 needs to yield to navigate over a previously advanced guidewire. In contrast, it is also desirable to have a distal tip region 50 that has high column strength in order to cross occluded and tight lesions within a vasculature. In addition, catheters 10 more easily track and navigate over narrow guidewires than thicker guidewires. The distal tip region 50 of a catheter 10 can more easily yield and turn with a thinner guidewire that is also yielding. Thicker guidewires possess increased stiffness. Increased stiffness prohibits an advancing catheter 10 from easily navigating the twists and turns of a human vasculature. Thus, it is desirable to manufacture a distal tip region 50 that is flexible for tracking through the vasculature, yet includes enhanced column strength for crossing tight lesions. It is additionally desirable to manufacture a catheter 10 that contains a distal tip opening suited for thinner guidewires, yet is expandable to accommodate thicker guidewires in certain circumstances. FIGS. 2-6 disclose embodiments of the present invention being convertible from a first outer diameter to a second outer diameter, and having a longitudinally stiff, while tangentially flexible, distal tip region 50.

FIGS. 2A and 2B depict two configurations of a preferred distal tip region 50. The length of the inner tubular member 18 at the catheter's distal tip region 50 is exaggerated or shown without the distal balloon waist for illustrative purposes only. Often, the distal balloon waist 34 is positioned just proximal the distal-most end 62 of the catheter 10. In particular, FIG. 2A illustrates a distal end 22 of an inner tubular member 18 having a gradually tapered distal tip 60. FIG. 2B illustrates the same inner tubular member 18 as shown in FIG. 2A, however, the tapered distal tip 60 of the inner tubular member 18 has been expanded to accommodate a larger guidewire.

FIG. 2A specifically shows a preferred distal tip region 50 of the catheter 10 of FIG. 1, having a gradually tapered distal tip 60. Emerging from the tapered distal tip 60 is a guidewire 70 having a smaller outer diameter, such as 0.012 inches. The guidewire 70 is shown in phantom. The tolerance between the inner diameter of the distal-most end 62 of the tapered distal tip 60 and the outer diameter of the guidewire 70 is minimal. The tolerance between the inner diameter of the inner tubular member 18 and the guidewire 70 proximal the distal tapering is significant when compared with that at the distal-most end 62 of the tapered distal tip 60.

In a preferred embodiment, the tapering of the distal tip region 50 of FIG. 2A is formed by cutting and removing at least one section of inner tubular member 18, as best illustrated in FIG. 2B. The enlarged distal tip 61 of FIG. 2B further illustrates the cutting configuration necessary to achieve the tapered distal tip 60 of FIG. 2A. A segment of inner tubular member 18 is removed having a wedge shape. The base of the wedge is the distal-most end 62 of the inner tubular member 18. The sides of the wedge taper inwardly as the sides move proximally from the distal-most end 62. The apex 64 of the wedge, therefore, is at a point proximal the distal-most end 62 of the inner tubular member 18. Multiple wedge sections covering less area may alternatively be removed around the diameter of the inner tubular member 18 to achieve the desired tapered configuration. Hereinafter, an inner tubular member 18 having a wedge of material removed from the distal most-end 62, as described in detail above, will be referred to as a "modified inner tubular member 66."

In one embodiment, a tapered distal tip 60 is formed from the modified inner tubular member 66 using a mandrel (not shown). The distal end of the mandrel preferably includes a tapered end. The modified inner tubular member 66 is loaded over the mandrel until the modified inner tubular member 66 is aligned with the mandrel's tapered end. The modified inner tubular member 66 is then held against the mandrel's tapered end forming a tapered distal tip 60. The tapered distal tip 60 includes at least one bonded section 68 having a single line of fissure where the walls of the modified inner tubular member 66 are positioned together. A shrink-wrap material is generally then placed over the tapered distal tip 60 in order to secure the modified inner tubular member 66 within the tapered configuration. The walls of the modified inner tubular member 66 are then adhesively or thermally bonded together in order to maintain the tapered configuration. The shrink-wrap is then removed, if originally applied, forming the final tapered distal tip 60.

The formed tapered distal tip 60 of FIG. 2A, however, may be made to fissure under the correct circumstances, discussed in detail below. In particular, the insertion of a guidewire 72 having a diameter greater than the smaller or 0.012-inch wire may be used to break the bonded section 68 of modified inner tubular member 66.

Materials may be added to the inner tubular member 18 to increase column stiffness without decreasing flexibility within the distal tip region 50. In one embodiment, the section of inner tubular member 18 forming the tapered distal tip 60 may be longitudinally striped with various blends of polymeric materials. In particular, the inner tubular member 18 may include several longitudinally extruded materials varying in relative stiffness. Alternating a stiff polymeric material next to a flexible polymeric material provides enhanced column support without significantly decreasing flexibility within the striped area.

In another embodiment, the alternating polymeric materials may be extruded in a spiral configuration. A twisting polymeric extrusion having different durometers resists compression and, therefore, increases column strength without significantly decreasing flexibility in the distal tip region 50.

In yet another embodiment, additional reinforcing filamentous materials may be added to the distal tip region 50 of the catheter 10. Stainless steel, nitinol and polymeric filaments can be added to the extruded inner tubular member 18 to increase column stiffness without significantly decreasing flexibility.

FIG. 2B is a partial perspective view of the preferred distal tip region 50 of FIG. 2A, having a larger diameter guidewire, such as a 0.014- or 0.018-inch guidewire 72, inserted therein. As described above, the inner tubular member 18 includes a diameter that permits a larger guidewire 72 (shown in phantom) to be slidably disposed therein. A larger guidewire 72, however, may not traverse the opening distal-most end 62 of the tapered distal tip 60 shown in FIG. 2A. The distal-most end 62 of the tapered distal tip 60 in FIG. 2A generally only permits a smaller guidewire, such as a 0.012-inch guidewire 70, to slidably pass therethrough. The advancing larger guidewire 72 possesses an outer diameter greater than the size of this opening at the distal most end 62.

When the advancing larger guidewire 72 contacts the tapered section of the tapered distal tip 60, the force applied by the guidewire 72 spreads apart the bonded section 68 forming the distal taper. Initial opening of the bonded section 68 along its line of fissure generally occurs at the distal-most end 62 of the tapered distal tip 60. The bond 68 then opens from this location proximally until the larger guidewire 72 may pass therethrough. The bond 68, therefore, may not necessarily be entirely fissured or broken.

After a portion of the bond 68 forming the distal taper is broken, the outer diameter of the modified inner tubular member 66 forming the tapered distal tip 60 is generally equivalent to the outer diameters of the other sections of inner tubular member 18 throughout the shaft assembly 12. As described above, however, the bond 68 need not necessarily open entirely to permit the passage of the larger guidewire 72. The enlarged tapered distal tip 61 may still impart a slight taper caused by the unbroken portions of the bond 68. Whether opened entirely or not, the larger guidewire 72 is now capable of being easily advanced past the opening at the distal-most end 62 of the enlarged distal tip 61.

Once the bond 68 forming the tapered distal tip 60 is opened, the opening at the distal-most end 62 generally remains in the opened configuration. In an alternative embodiment, however, an elastomeric sleeve (not shown) may be placed over the bonded segment 68 forming the tapered distal tip 60 shown in FIG. 2A. The elastomeric sleeve imparts a constricting pressure on the surrounding modified inner tubular member 66, forcing the tapered distal tip 60 to return to a tapered configuration if the larger wire is removed. When a larger guidewire 72 opens the bonded segment 68 enlarging the tapered distal tip section 61, the elastomeric sleeve permits an enlargement only necessary for the guidewire 72 to be slidably displaced therethrough. Once the larger guidewire 72 is removed, the elastomeric sleeve constricts the enlarged distal tip section 61 into its original tapered configuration 60. This embodiment is particularly useful for re-crossing stents and stenotic regions where an enlarged distal tip section 61 may cause the distal-most end 62 of the catheter 10 to be "hung-up" on the stent or surrounding tissue.

FIGS. 3A and 3B are cross-sections of the embodiments of FIGS. 2A and 2B along the lines 3A-3A and 3B-3B, respectively. Lines 3A-3A and 3B-3B traverse the distal tip region 50 of their respective views. The cross-sectional view of FIG. 3A shows the narrow tolerance between the smaller guidewire 70 and the walls of the inner tubular member 18. This cross-sectional view further shows the disruption of continuity in the wall of the inner tubular member 18. In particular, the bonded line of fissure 68 is shown where the wall of the inner tubular member was cut to form the tapered distal tip configuration 60 of FIG. 2A.

FIG. 3B additionally shows the disruption of the continuity in the wall of the inner tubular member. The larger guidewire 72 is shown having opened the bonded line of fissure 68 forming the tapered distal tip configuration 60 of FIG. 2A. The cross-sectional view particularly shows the large gap 74 in the wall of the inner tubular member 18. The gap 74 is sufficiently large enough to enlarge the distal tip 61, but narrow enough not to permit the guidewire 72 from escaping the lumen that inner tubular member 18 defines.

The use of multiple wedges (not shown) forming the modified inner tubular member 66 can further confine the guidewire 72 within the inner tubular member lumen 18. Multiple wedges individually remove less tubular material, thereby limiting the size of any single gap 74 in the wall of the inner tubular member 18. Reducing the size of a gap 74 additionally reduces the possibility that the guidewire 72 may extend through that gap 74.

Refer now to FIG. 4, wherein an alternative embodiment for the distal tip region 50 of the catheter 10 of FIG. 1 is shown. The tapered distal tip 63 is formed by making a lateral cut 76 into the larger inner diameter inner tubular member 18. The lateral cut 76 extends from the distal-most end 62 of the inner tubular member 18 proximally to a point distal from the waist of the balloon 34. Unlike the embodiment depicted in FIG. 2A, however, a wedge-shaped section is not removed from the inner tubular member 18 in FIG. 4.

Forming the distal tip region 50 in FIG. 4 can be accomplished by the use of a mandrel (not shown). The mandrel is advanced through the inner tubular member 18 until the distal tip of the mandrel emerges from the distal-most end 62 of the catheter 10. In preferred embodiments, the distal tip of the mandrel includes a slight tapering. The portions of inner tubular member 18 adjacent the lateral cut 76 are then overlapped, seen in phantom, to conform to the tapering of the mandrel. The overlapped portions of inner tubular member 18 are then shrink-wrapped and processed using thermal techniques to impart a tapered distal tip 63. The shrink-wrap is then removed from the tapered distal tip 63 and the mandrel is withdrawn from the catheter 10. The processed tapered distal tip 63 of FIG. 4 includes an opening at the distal-most end 62 having an inner diameter such as 0.012 inches or greater to accommodate a smaller guidewire. The inner diameter proximal the opening at the distal-most end 62 gradually tapers from the smaller diameter to a larger diameter, such as an inner diameter that accommodates a 0.014-inch, 0.018-inch, or 0.035-inch guidewire 72. It is also noted that FIG. 4 discloses inner tubular member 18 including two portions joined under the balloon waist 34 by a butt joint 19, with the distal portion 21 forming the tip 63.

In operation, a physician advances the catheter 10 in FIG. 4 over a smaller diameter guidewire 70. When the physician comes across a particularly difficult occlusion to cross, the physician withdraws the smaller guidewire 70 and advances a larger guidewire 72 through the positioned catheter 10. Tubular support is imparted to the catheter 10 as the larger diameter guidewire 72 approaches the distal-most end 62 of the catheter 10. After reaching the tapered distal tip 63 of the catheter 10, the physician applies a greater advancing pressure upon the guidewire 72 to fissure the processed tapered distal tip 63. When the processed tapered distal tip 63 is fissured, the lateral cut 76 opens to its original or larger inner diameter. The larger guidewire 72 is then fully advanced through opening at the distal-most end 62. With the added distal tubular support, the catheter 10 may cross tight or totally occluded lesions within the vasculature.

Expanding the processed tapered distal tip 63 may be a non-reversible occurrence. After expansion, the enlarged distal tip can remain with the larger inner diameter configuration for the remainder of the operation. In one embodiment, however, an elastomeric sleeve (not shown) may be secured over the tapered distal tip 63 in FIG. 4. The elastomeric sleeve imparts a constricting force upon the diameter of the inner tubular member 18. When the tapered distal tip 63 is expanded, the elastomeric sleeve counteracts the increased diameter profile of the tapered distal tip 63. In certain embodiments, once the larger guidewire 72 is withdrawn and replaced with a smaller guidewire 70, the elastomeric sleeve reduces the profile of the enlarged distal tip to its originally processed configuration.

FIG. 5 shows another embodiment of the present invention having a distal tip region 50 incorporating a rigid polymeric insert 82. Column stiffness within the distal tip region 50 permits the catheter 10 to more easily cross difficult lesions and occlusions. It is generally undesirable, however, to have an entire distal tip region 50 comprising stiff polymeric material. Navigation through a patient's tortuous vasculature increases in difficulty with increased distal tip stiffness. Therefore, unlike the previously described embodiments, the embodiment in FIG. 5 incorporates a rigid insert 82 whose structure may be varied to increase column stiffness within specific desired regions of a catheter's distal tip 80. Only specific areas within the distal tip 80 are desired to be made rigid for heightened column support. The remaining portions of the distal tip 80 will remain quite flexible for enhanced navigation and trackability within a patient's vasculature. A rigid insert 82 allows for such selectability. The materials, shapes and sizes of the rigid insert 82 may all be modified to accommodate specific vascular applications.

Rigid insert 82 is generally made of stiff polymeric materials. Materials suitable for the rigid polymeric insert 82 include nylon and similar polyamides such as Grilamid or Vestamid, as well as other rigid polymers such as polyetheretherketone (PEEK), polyimide (PI), and polyetherimide (PEI). In alternative embodiments, the stiffness within the rigid insert 82 is modified by altering the composition within the rigid insert 82. For example, materials may be added to the rigid insert 82 to increase column stiffness while enhancing flexibility. In one embodiment, the rigid insert 82 may be longitudinally striped with various blends of polymeric materials. In particular, the rigid insert 82 may include several longitudinally extruded materials varying in relative stiffness. Alternating a stiff polymeric material next to a flexible polymeric material provides enhanced column support without significantly decreasing flexibility within the striped area of the rigid insert 82.

In another embodiment, the alternating polymeric materials forming the rigid insert 82 may be extruded in a spiral configuration. A twisting polymeric extrusion having varying durometers resists compression and, therefore, increases column strength. This increase in column strength occurs without significantly decreasing flexibility of the rigid insert 82, as well as the entire distal tip region 50 as a whole.

In yet another embodiment, additional reinforcing filamentous materials may be added to the rigid insert 82. Stainless steel, nitinol and polymeric filaments can be added to a less stiff polymeric material to form a rigid insert 82. This embodiment forms a rigid insert 82 imparting increased column stiffness without significantly decreasing flexibility.

The rigid insert 82 is generally pre-shaped to mimic the profile of a lumen within a catheter 10. Specifically, the rigid insert 82 is shaped to conform to the lumens within the distal tip region 50 of the catheter 10. In one embodiment, specifically illustrated in FIG. 5, the distal end of the rigid insert 82 is positioned at the distal-most end 62 of the distal tip 80. The rigid insert 82 extends proximally from the distal-most end 62 of the catheter 10 to a point proximal the distal end of the balloon waist 34. The size of the rigid insert 82 may be reduced significantly to increase flexibility within the distal tip region 50 for navigation and trackability purposes. The lengths and sizes of the rigid insert 82, therefore, may be easily varied without deviating from the spirit and scope of the invention. For example, in an alternative embodiment, a supple polymeric material (not shown) is positioned distal the rigid insert 82. This configuration permits the supple polymeric material to act as an atraumatic distal tip. The formation of an atraumatic distal tip, in combination with a rigid insert 82, fails to affect the column stiffness caused by the introduction of the rigid insert 82 within the distal tip region 50 of the catheter 10.

The initial inner diameter of the rigid insert 82 generally accommodates the passage of a smaller guidewire, such as a 0.012-inch guidewire 70. In a preferred embodiment, the rigid insert 82 abuts the inner tubular member 18, forming a continuous, uninterrupted inner lumen that extends to the distal-most end 62 of the catheter 10. In an alternative embodiment, the rigid insert 82 is fitted over the inner tubular member 18. In yet another embodiment, the rigid insert 82 is fitted within the lumen formed by the inner tubular member 18.

FIG. 5 specifically shows a butt joint formed between the rigid insert 82 and the inner tubular member 18, wherein the rigid insert 82 abuts the end of inner tubular member 18. If the rigid insert 82 is fitted either over or under the inner tubular member 18, a lap joint must be formed. The lap joint seals the portion of overlap between the two structural elements. Sealing the two structural elements together ensures fluid continuity and structural integrity within the distal tip region 50 of the catheter 10. When lap joints are formed, a polymeric backfill may be added to the lap joint to smooth the transition between the various structural elements. Backfilling the lap joint, in particular, permits an advancing guidewire 70 or 72 to cross easily over the joint without resistance. An advancing catheter 10 generally experiences resistance when the lap joint is particularly disjointed. In the present case, disjointedness occurs most frequently when a thick walled rigid insert 82 is fitted within the inner tubular member 18. Backfilling is needed less when the rigid insert 82 is fitted over the inner tubular member 18.

Although the rigid polymeric insert 82 is generally stiff, the insert 82 may expand radially. Expansion of the rigid insert 82 is often aided by various manufacturing techniques. In a preferred embodiment, a longitudinal slit 84 is imparted along the length of the rigid insert 82. In alternative embodiments, multiple longitudinal slits 84 are imparted along the length of the rigid insert 82. The rigid insert 82, as described above, may comprise any selected material. In general, however, all the materials suitable for the rigid insert 82 permit a degree of compliance to conform to a newly expanded configuration.

Expansion of the distal tip 80 occurs when a guidewire 72 of a greater diameter, such as a 0.014-inch, a 0.018-inch, or a 0.035-inch guidewire, is advanced through the inner tubular member 18. As the larger guidewire 72 enters the region including the rigid insert 82, the rigid insert 82 radially expands to accommodate the larger guidewire 72. The distance between longitudinal slits 84 opens until the guidewire 72 may cross the entire length of the insert 82. The guidewire 72 is then further advanced until the guidewire 72 exits the catheter 10. When the larger guidewire 72 is withdrawn from the catheter 10, the rigid insert 82 may or may not reduce its diameter profile to its original configuration. In particular embodiments, an elastomeric sleeve 86 is disposed over the length of rigid insert 82 to reduce the outer diameter of the insert 82 after guidewire 72 withdrawal. Controlling the radial expansion of the rigid insert 82 is of particular importance when re-crossing stents and stenotic regions where an expanded distal tip 80 may cause the distal end of the catheter to be "hung-up" on the stent or surrounding tissue.

Material selection for the elastomeric sleeve 86 includes those materials having desirable expansion and compliance characteristics. The elastomeric sleeve 86 needs to be capable of expanding to a radial diameter, and furthermore, retracting back to the generally same initial diameter. Materials suitable for the elastomeric sleeve 86 include generally flexible thermoplastic materials. In preferred embodiments, the elastomeric sleeve 86 is comprised of polyamide, polyether elastomer, ethylene vinyl acetate (EVA), polyurethane, or latex, as well as other suitable thermoplastic elastomers. Specific polymers can include PEBAX, Tecothane or Grilamid.

In embodiments having the rigid insert 82 inserted under the inner tubular member 18, the stiffness of the inner tubular member 18 may reduce the outer diameter of the rigid insert 82 back to into original configuration. In alternative embodiments, as well as the one previously mentioned, the elastomeric sleeve 86 controls the uniform rate of expansion and contraction of the rigid insert 82. In many instances, the materials forming the elastomeric sleeve 86 and the inner tubular member 18 generally fail to bond with the materials forming the rigid insert 82. In order to obtain proper adhesion between the dissimilar materials, other mechanical means must be utilized for bonding purposes. In a preferred embodiment, a mechanical lock 92 is formed between the elastomeric sleeve 86 or inner tubular member 18 and the rigid insert 82.

During manufacturing, a plurality of holes 88 is milled through the walls of the rigid insert 82. The plurality of holes 88 generally extends along the entire length and circumference of the rigid insert 82. The size of holes 88 milled generally depends upon the desired application of the catheter 10, and the materials used in forming the elastomeric sleeve 86 or inner tubular member 18. The modified rigid insert 82 is then inserted over a mandrel. The outer diameter of the mandrel forms a tight friction fit with the inner diameter of the modified rigid insert 82. The polymeric material used to form the elastomeric sleeve 86 or inner tubular member 18 overlays the modified rigid insert 82 and mandrel. The polymer, when heated, flows into each of the holes 88 previously milled into the rigid insert 82. When the elastomeric polymer hardens, the mandrel is removed.

The inserted sectional view 90 of FIG. 5 best illustrates the resulting mechanical lock between the two dissimilar materials. Section 90 shows the phantom removal of a portion of rigid insert 82. "Fingers" 92 of polymeric material are shown extending down from the body of the inner tubular member 18 into the spaces where holes 88 would be located though the rigid insert 82. These fingers 92 fill the annular space of the holes 88 preventing the longitudinal displacement between the rigid insert 82 and the inner tubular member 18. Furthermore, the fingers 92 often anchor the inner tubular member 18 to the rigid insert 82, thereby also preventing the vertical displacement between the rigid insert 82 and inner tubular member 18.

Refer now to FIG. 6, wherein an alternative embodiment for the distal tip region 50 of the catheter 10 of FIG. 1 is shown. The distal tip region 50 is formed similarly to those embodiments utilizing a rigid polymeric insert 82 as described in reference to FIG. 5. As such, the placement, length, materials of the insert 94 of FIG. 6 are similar to those described above, however, unlike the previous embodiments, the present embodiment incorporates a helical cut into the rigid insert 94.

In one preferred embodiment, as depicted in FIG. 6, the helically cut rigid insert 94 proximal portion is fitted under the distal balloon waist 34 and abuts the distal end of the inner tubular member 18 so that a lap joint 96 is formed at the rigid insert's most proximal end by the distal waist 34. This is preferably the only attachment site for the helically cut rigid insert 94. Anchoring the proximal portion of the helically cut rigid insert 94 with the distal portion extending beyond the distal balloon waist 34 allows those portions of the rigid insert to move freely. The helically cut rigid insert 94 may bend in any direction by displacing the "windings" 98 forming the helically cut rigid insert 94. The helically cut rigid insert 94 is depicted in an expanded state, allowing passage of a larger wire. In a preferred embodiment, the distal portion would be formed with a tapered portion which expands as the larger wire passes therethrough. Alternatively, the helically cut rigid insert 94 can be fit within the inner tubular member 18, with this design additionally reducing the opening at the distalmost end 62 of the distal tip region 50 to an inner diameter that accommodates the passage of a smaller guidewire 70, such as a 0.012-inch wire.

Expansion of the distal tip region 50 incorporating a helically cut rigid insert 94 occurs when a guidewire 72 of a larger diameter, such as 0.014 inches or 0.018 inches, is advanced through the inner tubular member 18. As the larger guidewire 72 enters the region including the helically cut rigid insert 94, the windings 98 of the rigid insert 94 displace. More specifically, the windings 98 slide along one another, expanding at least a portion of the helically cut rigid insert 94 from a first diameter to a second diameter. When the larger guidewire 72 is withdrawn from the catheter 10, the helically cut rigid insert 94 similarly reduces its diameter profile to its original configuration by unwinding the helically cut rigid insert 94.

In particular embodiments, an elastomeric sleeve 86 is disposed over the length of helically cut rigid insert 94 to reduce the outer diameter of the insert 94 after guidewire 72 withdrawal. Controlling the radial expansion of the helically cut rigid insert 94 is of particular importance when re-crossing stents and stenotic regions where an expanded distal tip section 50 may cause the distal end of the catheter 10 to be "hung-up" on the stent or surrounding tissue.

Material selection for the elastomeric sleeve 86 includes those materials having desirable expansion and compliance characteristics. The elastomeric sleeve 86 needs be capable of expanding to a radial diameter and, furthermore, retracting back to the generally same initial diameter. Materials suitable for the elastomeric sleeve 86 include generally flexible thermoplastic materials. In preferred embodiments, the elastomeric sleeve 86 is comprised of polyamide, polyether elastomer, ethylene vinyl acetate (EVA), polyurethane, or latex, as well as other suitable thermoplastic elastomers. Specific polymers can include PEBAX, Tecothane or Grilamid.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is of course defined in the language in which the appended claims are expressed.

What is claimed is:

1. A balloon catheter assembly comprising:
    an outer tubular member having a proximal end and a distal end;
    an inner tubular member having a proximal end and a distal end with a lumen extending therethrough, the inner tubular member having a first column stiffness;
    an expandable tubular member having a proximal end and a distal end, the expandable tubular member disposed proximate the distal end of the inner tubular member and extending distally therefrom, the expandable tubular member having a second column stiffness greater than the first column stiffness, wherein the expandable tubular member is expandable from a first inner diameter to a second inner diameter; and
    an inflatable balloon having a proximal end affixed proximate the distal end of the outer tubular member, and a distal end affixed proximate the distal end of the expandable tubular member.

2. The balloon catheter assembly of claim 1, wherein the inner tubular member is coaxially disposed within the outer tubular member.

3. The balloon catheter assembly of claim 1, wherein the proximal end of the expandable tubular member is disposed adjacent to the distal end of the inner tubular member.

4. The balloon catheter assembly of claim 1, wherein the expandable tubular member includes a longitudinally extending slit along at least a portion of a length of the expandable tubular member.

5. The balloon catheter of assembly of claim 4, where the expandable tubular member includes a plurality of longitudinally extending slits along at least a portion of the length of the expandable tubular member.

6. The balloon catheter assembly of claim 1, wherein a flexibility of the inner tubular member and a flexibility of the expandable tubular member are approximately the same.

7. The balloon catheter assembly of claim 1, further comprising an elastomeric sheath disposed at least in part over the expandable tubular member.

8. The balloon catheter assembly of claim 1, wherein the expandable tubular member further comprises a plurality of holes.

9. The balloon catheter assembly of claim 1, wherein the expandable tubular member further comprises reinforcing filaments extending longitudinally along at least a portion of the length of the expandable tubular member.

10. The balloon catheter assembly of claim 1, wherein the distal portion of the expandable tubular member expands from an inner diameter of about 0.012 inches to an inner diameter of about 0.024 inches.

11. A balloon catheter assembly comprising:
- an inflatable member having a proximal end and a distal end;
- a first tubular member having a proximal end, a distal end, and defining a lumen therethrough, the first tubular member extending through at least a portion of the inflatable member; and
- a second tubular member having a proximal end, a distal end, and defining a lumen therethrough, the proximal end of the second tubular member abutting the distal end of the first tubular member, and the second tubular member including means for expanding from a first outer diameter to a second outer diameter; and
- wherein the second tubular member includes two or more polymeric material; and
- wherein the first tubular member comprises a first column stiffness and the second tubular member comprises a second column stiffness greater than the first column stiffness.

12. The balloon catheter assembly of claim 11, wherein the means for expanding from a first inner diameter to a second inner diameter includes at least one longitudinal slit extending along at least a portion of a length of the second tubular member.

13. The balloon catheter assembly of claim 11, wherein the two or more polymeric materials vary in relative stiffness.

14. The balloon catheter of claim 11, wherein the lumen of the first tubular member and the lumen of the second tubular member are generally aligned.

15. The balloon catheter of claim 11, further comprising an elastomeric sheath disposed over at least a portion of the second tubular member.

16. The balloon catheter of claim 15, wherein the elastomeric sheath is configured to bias the second tubular member towards the first outer diameter.

17. A balloon catheter assembly comprising:
- an outer tubular member having a proximal end and a distal end;
- an inner tubular member having a proximal end, a distal end, and defining a lumen therethrough, the inner tubular member having a first stiffness and a first flexibility;
- a polymeric insert having a proximal end, a distal end, and defining a lumen therethrough, the proximal end of the insert disposed adjacent to the distal end of the first tubular member, and the insert including means for expanding from a first outer diameter to a second outer diameter; and
- an inflatable balloon having a proximal end affixed proximate the distal end of the outer tubular member, and a distal end affixed proximate the distal end of the insert wherein the polymeric insert has a second stiffness greater than the first stiffness and a second flexibility similar to the first flexibility.

* * * * *